United States Patent [19]
Blount

[11] Patent Number: 5,691,436
[45] Date of Patent: Nov. 25, 1997

[54] PRODUCTION OF SILICON-PHOSPHORUS CONTAINING COMPOSITIONS

[76] Inventor: David H. Blount, 6728 Del Cerro Blvd., San Diego, Calif. 92120

[21] Appl. No.: 767,416

[22] Filed: Dec. 16, 1996

Related U.S. Application Data

[63] Continuation-in-part of Ser. No. 680,651, Jul. 16, 1996, Pat. No. 5,693,840.

[51] Int. Cl.$^6$ .................... C07F 7/08; C07F 7/10
[52] U.S. Cl. .................... 528/26; 528/26.5; 528/27; 528/28; 528/29; 556/402; 556/404; 556/405; 556/9; 556/12; 554/77; 554/75; 548/402; 548/403; 548/405; 548/406; 549/483; 549/505; 540/486; 540/487
[58] Field of Search ............... 528/26, 25.5, 28, 528/27, 29; 556/402, 404, 405, 9, 12; 554/75, 77; 548/402, 403, 405, 406; 549/483, 505; 540/486, 487

[56] References Cited

U.S. PATENT DOCUMENTS

| | | | |
|---|---|---|---|
| 4,389,530 | 6/1983 | Arit et al. | 556/404 |
| 4,523,009 | 6/1985 | Neilson et al. | 556/404 X |
| 5,082,958 | 1/1992 | Wright et al. | 556/404 X |
| 5,563,285 | 10/1996 | Blount | 556/404 |

*Primary Examiner*—Paul F. Shaver

[57] ABSTRACT

A mixture of silicon and phosphorus are heated and reacted with halide to produce silicon tetrahalides, silicon-phosphorus halide and phosphorus trihalides compositions. These compositions are reacted with any suitable organic, inorganic-organic and/or inorganic compound to produce novel organic silicon-phosphorus containing compositions. These compositions may be utilized as flame retardants, coating agents, adhesives and many other uses.

21 Claims, No Drawings

PRODUCTION OF SILICON-PHOSPHORUS CONTAINING COMPOSITIONS

This application is a continuation-in-part of Pat. No. 08/680,651, filed Jul. 16, 1996, now Pat. No. 5,693,848.

This invention concerns novel compositions containing silicon and phosphorus atoms and their preparation and use. These novel compounds may contain a plurality of silicon atoms or a plurality of phosphorus atoms. These compounds may be utilized as flame-retardants, insecticides, hydraulic fluid, adhesives, coating agents, polymers, plastics, and many other uses.

BACKGROUND

The production of silicone compounds and organic phosphorus containing compounds are well known in the arts. The utilization of silicon-phosphorus and their halide reaction products to produce novel silicon-phosphorus halide compounds and novel organic silicon-phosphorus compositions, polymers and products is new. The organic silicon-phosphorus compounds and polymers have novel and desirable properties which decrease flammability and smoke production when these products are burned. These compounds, polymers and products have many uses such as reactants to produce novel compounds, polymers and plastics, as a flame-retardant in plastics, as a lubricant, as hydraulic fluid, as an adhesive, as a coating agent, as a rust inhibitor, as building materials, foamed to produce insulation and sound proofing and many other uses. The phosphorus halide are highly active compounds and will readily react with inorganic and organic compounds. The silicon halide are not as active but their activity is greatly increased in the presence of phosphorus halide and will react with phosphorus halide, organic phosphorus compounds and many inorganic and organic compounds.

The object of this invention is to provide silicon-phosphorus halide compositions which are utilized to produce inorganic silicon-phosphorus halides, organic silicon-phosphorus halides compounds and polymers, organic silicon-phosphorus compounds, polymers and products.

SUMMARY

The invention comprises silicon-phosphorus compounds, silicon-phosphorus halides, silicon-phosphorus halides reaction compositions and their reaction products with organic and/or inorganic compounds. Another aspect of the invention is a process to produce silicon-phosphorus halide and the process to react these compounds with organic and/or inorganic compounds to produce organic silicon-phosphorus halide and organic silicon-phosphorus containing compositions which utilize the following components:

A. silicon compound

B. phosphorus compound

C. halide compound.

Components A, B and C are reacted to produce silicon-phosphorus halides compounds, silicon tetrahalide and phosphorus trihalide, which are reacted with:

D. organic compound in an amount to wherein there are halogen atoms and/or radical with active hydrogen or metal left on the compound thereby producing an organic silicon-phosphorus containing compound; then reacted with E. saturated or unsaturated organic compound, Grignard reagent and/or organio-metallic compound that will react by condensation or addition with the organic silicon-phosphorus containing compound thereby producing a resinous composition; then electively with F. basic salt forming compound; then electively with G. water; then H. polymerize by any means that will complete the polymerization to produce an organic silicon-phosphorus containing resinous composition.

The sequence of the addition of the components A, B, C, D, E,F and G may be varied depending on the end product desired. In the production of silicon tetrahalide and phosphorus halide reaction compounds, the halide may be reacted separately with the silicon compound, and separately with the phosphorus compound then the silicon halide reaction compounds are mixed with the phosphorus halide reaction compounds. This mixture is then reacted with an organic compound, in an amount wherein halide atoms are left on the silicon and/or phosphorus atoms, to produce an organic silicon-phosphorus halide composition. This composition is then reacted with more organic an/or inorganic compounds to produce organic silicon-phosphorus containing products. The silicon-phosphorus halide mixture may be reacted with an amount of organic compound to produce organic silicon-phosphorus containing compounds, polymers and products.

In another process the silicon compound may be mixed with the phosphorus compound, then reacted with a halide compound to produce a composition of silicon halide, phosphorus halide and silicon-phosphorus halide which are then reacted with an organic and/or inorganic compound. In another method the halide compound is reacted with an organic compound, and then reacted with a mixture of silicon and phosphorus compounds to produce organic silicon-phosphorus containing compositions. In another method the organic compound is reacted with halide compounds to produce and organic halide, which is then reacted with a metal compound to produce a metal organic halide (Grignard reagent). The metal organic halide compound is then reacted with the mixture of silicon tetrahalide and phosphorus halide to produce organic silicon-phosphorus containing compositions. In another method a metal is reacted with an organic compound to produce a metal organic compound, which is then reacted with the reaction product of component A, B and C to produce and organic silicon-phosphorus halide and/or an organic silicon-phosphorus containing composition. In another method the silicon halide may be reacted with an organic compound to produce an organic tri or di-chlorosilane compound, and the phosphorus halide may be reacted with an organic compound to produce an organic phosphorus halide compound, then these compounds are mixed, and reacted with an organo-metal compound to produce organic silicon-phosphorus containing compounds, polymers and products. The organic silicon-phosphorus halide may be reacted with water and or basic salts to produce organic silicon-phosphorus containing compounds, polymers and products.

The silicon tetrahalide, phosphorus trihalides and silicon-phosphorus halide compositions may also be produced by mixing powdered silica, phosphorus or alkaline earth metal phosphates and carbon or a metal such as magnesium, then heating the mixture to a high enough temperature in an electric furnace to where the carbon combines with the oxygen thereby producing a mixture of silicon-phosphorus, phosphorus and silicon. An excess amount of halogen atoms or compounds are passed through this hot mixture thereby producing a mixture containing silicon tetrahalide, silicon-phosphorus halide and phosphorus halide. Phosphorus is commercially produced from a mixture of calcium phosphate, silica and carbon by heating the mixture. The phosphorus is recovered by distillation. Silicon is commercially produced from a mixture of silica and carbon. This mixture is heated in an electric furnace and the carbon reacts with the oxygen on the silica, and silicon and carbon dioxide are produced.

The phosphorus trihalide, silicon-phosphorus halide (Si—P halides) and silicon tetrahalide may be modified by the addition of water in the amount of 1–2 mols to one mol of phosphorus trihalide to produce a silicon-phosphorus oxyhalides composition. This Si—P halide mixture may also be modified by the addition of phosphorus pentaoxide in the amount of about 1 to 2 mols of phosphorus pentaoxide to 6 mols of phosphorus trihalide thereby producing a silicon-phosphorus oxyhalides composition. The organic compound may also be mixed with water then the Si—P halide (phosphorus trihalides, silicon-phosphorus halide and silicon tetrahalide) are slowly added while agitating to produce organic silicon-phosphorus containing compounds or polymers. The Si—P halide may also be first added to water then the organic compounds is added and reacted to produce an organic silicon-phosphorus containing compound, or the water may be added to the organic compounds.

Preferably, the phosphorus compound and silicon compound are mixed then reacted with a halide to produce a mixture of silicon halide, phosphorus halide and silicon-phosphorus halide, which are then reacted with an organic compound. Another very suitable method is to react the halide with the silicon and phosphorus compounds separately, then mix the two together, and then react the Si—P halide mixtures with organic compounds.

COMPONENT A

Any suitable silicon compound may be utilized in this invention such as silicon and silicon dioxide. Silicon in a powdered form is the preferred silicon compound in the production of silicon tetrahalide and silicon-phosphorus halide. Organic silicon halides and silicon halides may also be utilized. The organic silicon halides, preferably should contain at least 2 halogen atoms but preferably 3 halogen atoms. Examples of silicon-halides include but are not limited to the following compounds; silicon tetrachloride, silicon tetrabromide, silicon tetrafluoride, silicon tetraiodide, alkyl trihalosilane, dialkydihalosilane, aryl trihalosilane, etc.

COMPOUND B

Any suitable phosphorus compound may be utilized in this invention such as phosphorus, phosphorus trihalides, phosphorus oxyhalides, alkaline earth metal phosphates, alkali metal phosphates, phosphorus oxides and organic phosphorus halides. Phosphorus is the preferred phosphorus compound. Phosphorus halide may also be utilized such as phosphorus trichloride, phosphorus pentachloride, phosphorus tribromide, phosphorus pentabromide, phosphorus trifluoride, phosphorus pentafluoride, phosphorus triiodide, phosphorus oxyhalides and mixtures thereof. Phosphorus trichloride is the preferred phosphorus halides. Phosphorus oxychloride is the preferred phosphorus oxyhalide. Phosphorus oxides are utilized to react with the phosphorus trihalides to produce phosphorus oxyhalides or reacted with carbon to produce phosphorus. Alkaline earth metal phosphates and alkali metal phosphates are reacted with silica and carbon to produce phosphorus. It is well known in the arts that phosphorus halides will react with many types of organic and/or inorganic compounds.

COMPONENT C

Any suitable halide compound may be utilized in this invention such as chlorine, fluorine, bromide and iodine and mixtures thereof. Chlorine is the preferred halide compound. Carbonyl chloride (phosgene) may also be used. Hydrogen halide such as hydrogen chloride, hydrogen fluoride, hydrogen iodide and hydrogen bromide may also be utilized. Organic halides may also be used such as alkyl halides. The phosphorus trihalides and phosphorus oxytrihalides may also be used to react with the heated silicon.

COMPOUND D

Any suitable organic compound may be utilized in this invention. Any suitable organic compound that will react with a silicon halides, silicon-phosphorus halides and/or phosphorus halides may be utilized in this invention. Suitable organic compounds may be substituted, saturated or unsaturated or mixture thereof. Suitable compounds are organic and inorganic-organic compounds with one or more active hydrogen and/or halide and/or metal radicals. These compounds may be aliphatic, aromatic, aliphatic-aromatic, heterocyclic, inorganic-organic and mixtures thereof. Suitable organic compounds include, but are not limited to, alcohols, polyalcohols, epoxides, epihalohydrins, polyepoxides, carboxylic acids and anhydrides, polycaboxyl acids and anhydrides, isocyanates, polyisocyanates, thioalcohols, thiophenols, phenols, phenoplasts, aldehydes, halogenated alcohols and polyalcohols, halogenated organic acids and polycarboxyl acids, sulphonic acid chlorides, organic esters, organic ethers, thioethers, halomethyl compounds, ketones, nitriles, sulphonic acids, amines, polyamines, polyesteramide, amino compounds, aminoplasts, alkyl magnesium chloride, alkenes, alkynes, alkyl halide, organometallic compounds such as methyl magnesium chloride, dialky mercury, dialkyl zinc, dialkyl magnesium, alkali metal carboxylic acids and polycarboxylic acids, alkyloxy alkali metals, alkali metal cyanides, alkaline earth metal cyanides, calcium carbide, arylalkenes, organic polyenes, aminophenols, proteins, terpenes, oils, fats, amides, polyamides, imides, polyimides, organic phosphates, organic phosphites, organic phosphonates, organic phosphines and other organic phosphorus containing compounds, carbohydrates, lignin, cellulose, amino acids, arylalkynes, halogenated alkenes, aminoalcohols, organic carbonates, Grignard reagents, orgnao-metallic, etc. and mixtures thereof.

There are a large number of Grignard reagents produced commercially that will react with the silicon-phosphorus halides or organic silicon-phosphorus halide compounds to produce organic silicon-phosphorus containing compounds, polymers and resins. The Grignard reagents may be substituted, saturated and/or unsaturated. The unsaturated Grignard reagents may be reacted with the organic silicon-phosphorus halides then either polymerized by means of the unsaturated radicals or with another unsaturated organic compound to produce a resinous composition.

Any suitable organic compound containing the following radicals and mixtures thereof may be utilized in this invention:

—SH, —CH Cl, —CH Br, —CH I, —CN, —NO, —COCl,

—COBr, —SO Cl, —SO Br, —COOH, S OH, —COO, —SO,

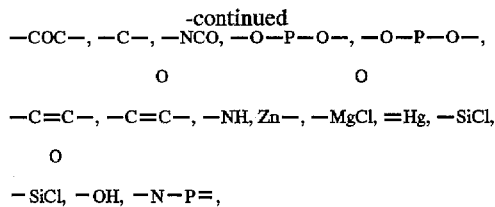

A more detailed list of suitable organic compounds may be found in "TEXTBOOK OF ORGANIC CHEMISTRY" by Carl R. Nooler, published by W. B. Saunders Co., 1966, Philadelphia and London, is incorporated herein by reference. A more detailed list of Grignard reagents may be found in FAR Research Catalog published by FAR Research, Inc. and ALDRICH TECH/CUST Catalog published by Aldrich and are incorporated herein by reference.

COMPONENT E

Any suitable substituted, saturated or unsaturated organic compound, organo-metallic compound and/or organo-metallic compound that will react with an organic silicon-phosphorus containing compound may be utilized in this invention. Suitable compounds include, but not limited to, substituted alcohols, unsaturated alcohols, chlorohydrin, polyhydroxyl compounds, glycolic acid, epoxides, polyepoxides, epihalohydrins, polycarboxylic acids and anhydrides, polyisocyanates, phenols, phenoplasts, polyhydroxy phenols, thiophenols, cresols, lignin, furans, aldehydes, polyether polyols, polyester polyols, polyesters with free acid radicals, aminoalcohols, polyamines, polyamides, alkenes, alkynes, arylalkenes, organic polyenes, cyclic unsaturated compounds, aromatic vinyl compounds, heterocyclic vinyl compounds, rosins, cellulose, statch, carbohydrates, proteins, alginic acid, polysulfide, thioplasts, coal tar, caprolactam, amino compounds, aminoplasts, terpenes, oils, fats, waxes, polyimides, ketones, furfuryl alcohol, acrylonitrile, organo-metallic compounds, Grignard reagents, alkali metal and alkaline earth metal salts of organic polycarboxylic acids.

COMPONENT F

Any suitable basic salt forming compound may be utilized in this invention. Suitable salt forming compounds include, but not limited to, compounds containing alkali metals, alkaline earth metals, metals and ammonia radicals, amines, polyamines, amino compounds, aminoplasts and mixtures thereof. Basic salt forming compounds may be in the form of metals, oxides, hydroxides, carbonates, bicarbonates, salts of organic acids, silicates, natural minerals, sulfur, alkali polysulfides, etc. and mixtures thereof.

COMPONENT G

Water may be utilized to react with the silicon tetrahalide and phosphorus trihalide to produce silicon-phosphorus oxyhalides and phosphorus oxytrihalides. 1–2 mols of water are added to each mol of phosphorus trihalide. Water may also be utilized to react with the organic silicon-phosphorus halide to produce organic silicon-phosphorus compositions. One mol of water is added for each mol of halide present on the organic silicon-phosphorus composition, but an excess of water may be used.

COMPONENT H

Any suitable polymerization means may be utilized to react the suitable organic compound with the organic silicon-phosphorus containing compound to produce a resinous composition. The polymerization may take place by condensation or addition process. Suitable means include heat, ultraviolet light, light, photochemical initiation, water, pressure, basic catalysts, Lewis acids, metal catalyst, free radical initiators, ionic catalyst, cationic catalyst, redox system and mixtures of the above polymerization means. A large number of organic and inorganic compounds form free radical upon decomposition act as initiators for vinyl polymerization. These compounds include the acyl and aryl peroxides and hyproperoxides, diazonium compounds and persulfates. Commonly known initiators are organic peroxides, such as benzoyl peroxide, methyl ethyl ketone peroxide, tert-butyl hydroperoxide, etc. Commonly known inorganic initiator are hydrogen peroxide, boron peroxide, etc. Promoters such as organic cobalt compounds, tertiary dialky aryl amines etc. and inhibitors may be used with the free radical initiators. Ionic initiators are compounds such as metal halides, which include stannic chloride, titanium tetrachloride, aluminum chloride, boron trifluoride, etc. Common anionic initiators are alkali metal amides, alkyl, and hydrides, alkali metals, Grignard reagents and alfin complexes. The polymerization means are well known in the Art.

DETAILED DESCRIPTION OF THE INVENTION

The chemical reactions that take place in this invention may take place in any suitable physical condition. Ambient pressure is usually satisfactory except when a gas compound is used, then it may be necessary to compress the gas until it is in the form of a liquid or mixed with a liquid such as water, liquid alkanes, liquid aromatics, alkylenes halide etc. In reacting the halide with silicon and phosphorus an elevated temperature is usually necessary. Silicon will react with dry chlorine at about 200–300 degrees C., and phosphorus will react with dry chlorine when in a molting stage. Temperatures up to 700 degrees C. is required for phosgene to react with silicon to form silicon tetrachloride. The temperature may range from ambient temperature to 800 degrees C. In some reactions to produce organic silicon-phosphorus halide compositions and organic silicon-phosphorus containing compositions it is necessary to cool the reaction mixture, in others it is necessary to use elevated temperatures.

When a mixture of silicon and phosphorus is being reacted with a halide it is preferable for the silicon and phosphorus to be in a powdered form, and heated in an electric furnace to between the molting and boiling temperature of phosphorus, then dry halide gas is passed through the hot components. An excess of halide may be used, but at least 4 mols of halide for each mol of silicon and 3 mols of halide for each mol of phosphorus should be used. In most reactions of the mixture of silicon tetrahalide, silicon-phosphorus halide and phosphorus trihalide with organic compounds, the reaction is exothermic and cooling is required.

In general, the liquid silicon tetrahalide, silicon-phosphorus halide and phosphorus trihalide mixture, produced from a mixture of silicon, phosphorus and halide contains about 6–7 mols of halide for 1 mol of silicon and one mol of phosphorus; whereby the phosphorus atom still has valences available for further bonding. The bonding between the silicon and phosphorus atoms reduces the valences available for further bonding. The mixture may also contain phosphorus pentahalide. Bridging of the silicon moiety with the phosphorus is represented by the corresponding hyphen (Si—P) in the compound nomenclature.

Any suitable amount of silicon compound may be mixed with the phosphorus compound depending on the type of compounds desired. The amount of silicon may range from 10 to 100 parts by weight whereas the amount of phosphorus may range from 10 to 100 parts by weight. An excess of the halogen are used to pass through the hot powdered mixture of silicon and phosphorus. When hydrogen chloride is utilized to react with the silicon and phosphorus mixture an excess amount is used. At least 3 or 4 mols of hydrogen chloride are utilized for each mol of silicon to produce hydrogen silicon chlorides, hydrogen and silicon tetrachloride. The amount of halide needed depends on the ratio of silicon to phosphorus.

The ratio of organic compounds to that of the mixture of silicon halide, phosphorus halide and silicon-phosphorus halide may greatly vary depending on the composition or product desired. In the production of organic silicon-phosphorus halide composition, the amount of organic compound utilized would depend on the amount of halide radicals that were to be left on the organic silicon-phosphorus halide compound and the number of active hydrogens present on the organic compound. In general, 0.5 to one mol of the organic compound would be used for each halide atom present on the silicon-phosphorus halide, silicon tetrahalide and phosphorus trihalide molecules. In the production of organic silicon-phosphorus containing compositions, sufficient organic molecules are utilized to equal the atoms of halide present on the organic silicon-phosphorus halide compound. Suitable amount of organic compound may range from up to 300 parts by weight.

The organic silicon-phosphorus halide and organic silicon-phosphorus containing compositions of this invention may be further reacted with inorganic or organic compounds. When unsaturated radicals are present they may be reacted with other unsaturated organic radicals by use of heat, ultra violet light, catalyst or free radical initiators to form polymers. When the organic silicon-phosphorus containing compositions have one or more active hydrogens, halide or metal radicals it may be further reacted with compounds such as isocyanates, polyisocyanates, epoxides, polyepoxides, organic metal compounds, organic acid halide, polycarboxyl acids, polycarboxylic anhydrides, polyhydroxy alcohols, polyamines, and many other organic compounds by the process of condensation or addition by utilizing heat, ultra violet light, catalyst, light, pressure, etc..

The organic silicon-phosphorus halides composition may be reacted with water to produce organic silicon-phosphorus polymers. The water may be added in the amount of one mol of water to one mol of halide atom present at one time, then after the reaction is complete another mol of water is added till all the halide radicals have reacted with the water to produce hydrogen halide and organic silicon-phosphorus compounds or polymers. An excess of water may also be added at one time. The method used depends on the products desired. Many of the organic silicon-phosphorus containing compounds which are produced using alcohols, low molecule weight polyalcohol, organic acids and polycarboxyl acid are soluble in water.

The exact formula for the compounds and products produced in this invention is not known but there is a mixture of compounds produced when the halide react with a mixture of silicon compounds and phosphorus compounds. The liquid mixture contains silicon halide, phosphorus halide, and silicon-phosphorus halide. This Si—P halide mixture contains compounds of the general formulae of:

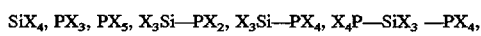

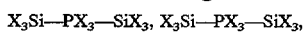

and other formulae depending on the ratio of Si to P. X is a halogen atom selected from the group consisting of chlorine, fluorine, bromide and iodine.

All of the formulae of the organic silicon-phosphorus halide compounds are not known but does contains compounds of the general formula of:

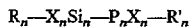

wherein n is a number 1–3, R and R' is an organic radical of the reaction products of the organic compounds which will react with silicon tetrahalides, silicon-phosphorus halides and/or phosphorus trihalide or phosphorus oxytrihalide and X is a halide selected from the group chloro, bromo, fluoro and iodo.

All of the formulae of the organic silicon-phosphorus compounds are not known but does contains compounds of the general formulae of:

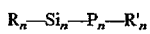

wherein n is a number 1–4, R and R' are organic radical of the reaction products of the organic compounds of which will react with silicon tetrahalide, silicon-phosphorus halide and/or phosphorus trihalide or phosphorus oxytrihalide.

All of the formulae of the organic silicon-phosphorus resinous composition are not known but does contains compounds of the general formulae of:

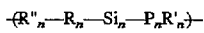

wherein n is a number 1–4, R is an organic radical that will react with an organic compound, R' is an organic radical that will react with an organic compound and R" is an organic compound with two or more radicals that will react with R and/or R'.

The silicon-phosphorus halide may also be produced by mixing powdered silicon dioxide, phosphorus oxides and carbon in a closed vessel is vented, the mixture is heated until the carbon reacts with the oxygen in the silicon dioxide and phosphorus oxides to form CO thereby producing silicon, phosphorus and silicon-phosphorus compositions, then a dry gaseous halide is passed through the hot silicon, phosphorus and silicon-phosphorus compositions until silicon-phosphorus halide, silicon tetrahalide and phosphorus trihalide are produced.

The ratio of the essential reactants and optional reactants which leads to the production of silicon-phosphorus containing compounds and compositions of this invention may vary broadly speaking, with ranges as follows:

A. 10 to 100 parts by weight of silicon compound;

B. 10 to 100 parts by weight of phosphorus compound;

C. 4 mols or more of halide for each mol of Si and 3 to 5 mols of halide for each mol of P; an excess of halide may be utilized;

D. 10 to 300 parts by weight of organic compound, and/or organo-metallic compound; or an excess of organic compound that will react with silicon halides, silicon-phosphorus halides and/or phosphorus halides;

E. 0 to 300 parts by weight of an organic compound and/or an organo-metallic compound that will react with an organic silicon-phosphorus halides or organic silicon-phosphorus containing compound with active hydrogens;

F. 0 to 100 parts by weight of a basic salt forming compound;

G. 0 to 400 parts by weight of water; or an excess of water;

H. a catalytic amount of the polymerization compounds;

I. one atom of carbon for each atom of oxygen present in the silicon oxides and phosphorus oxides.

DESCRIPTION OF PREFERRED EMBODIMENTS

The following examples which describe certain preferred embodiments of the processes may, of course, be varied as described above with similar results. Parts and percentages are by weight unless otherwise indicated.

EXAMPLE 1

Preparation of a silicon tetrahalide, phosphorus trihalide and silicon-phosphorus halide compositions:

A. About equal parts by weight of powdered silicon and phosphorus are mixed. The mixture is heated to just below the boiling point of phosphorus (200–400 degrees C.) in a closed vessel, then dry chlorine is passed through the hot mixture until a mixture of silicon tetrachloride, phosphorus trichloride and silicon-phosphorus halide composition are produced. At least 7 mols of chlorine are added to 1 mol of silicon and 1 mol of phosphorus;

B. About equal parts by weight of silicon tetrachloride and phosphorus trichloride are mixed;

C. About equal parts by weight of silicon tetrachloride and phosphorus oxychloride are mixed;

D. Example 1A is modified wherein two parts by weight of silicon is mixed with 1 part by weight of phosphorus;

E. Example 1A is modifies wherein one part by weight of silicon is mixed with 2 parts by weight of phosphorus.

EXAMPLE 2

About 50 parts by weight of methanol are added to a flask, and then placed in an ice bath; then 20 parts by weight of silicon tetrachloride, phosphorus trichloride, and silicon-phosphorus chlorides liquid composition of 1A is slowly added to the methanol while agitating and hydrochloric acid evolves. The excess methanol is evaporated off of the liquid organic silicon-phosphorus composition.

EXAMPLE 3

Example 2 is modified wherein about 1 mol of methanol is added with 3 mols of the chlorine present on the silicon tetrachloride, phosphorus trichloride and silicon-phosphorus halide mixture, thereby producing a liquid organic silicon-phosphorus chlorides containing composition.

EXAMPLE 4

Example 2 is modified wherein the silicon tetrachloride and phosphorus trichloride mixture of 1B is utilized in place of 1A.

EXAMPLE 5

Example 2 is modified wherein the silicon tetrachloride and phosphorus oxytrichloride mixture of 1C is utilized in place of 1A.

EXAMPLE 6

Example 2 is modified wherein the silicon tetrachloride, phosphorus trichloride and silicon-phosphorus chlorides composition of 1D is used in place of 1A.

EXAMPLE 7

Example 2 is modified wherein the silicon tetrachloride, phosphorus trichloride and silicon-phosphorus chlorides composition of 1E is used in place of 1A.

EXAMPLE 8

Example 2 is modified wherein another alcohol is used in place of methanol and is selected from the list below:

| | |
|---|---|
| a) ethanol | k) chlorohydrin |
| b) 1-propanol | l) phenol |
| c) 2-propanol | m) furfuryl alcohol |
| d) 1-butanol | n) dimethylethanolamine |
| e) 2-butanol | o) mixture of the above |
| f) 2-methyl-1-propanol | |
| g) 2-methyl-2-propanol | |
| h) 1-pentanol | |
| i) hexyl alcohol | |
| j) allyl alcohol | |

EXAMPLE 9

Example 2 is modified wherein a polyhydroxy compound is used in place of methanol and is selected from the list below:

| | |
|---|---|
| a) ethyl glycol | k) cellulose |
| b) propylene glycol | l) lignin |
| c) 1,4-butanediol | m) sucrose |
| d) glycerol | n) carbohydrate |
| e) 1,2,3-propanetriol | o) hydroquinone |
| f) 1,2,4-butanetriol | p) resorcinol |
| g) polypropylene glycol, mol wt. 400 | q) polyethylene glycol, mol wt. 200 |
| h) 1,2,10-decanetriol | r) polyester polyol |
| i) glucose | s) sucrose polyether polyol |
| j) glycerine | t) propylene polyether polyol |
| | u) and mixtures thereof |

EXAMPLE 10

Example 2 is modified wherein an epoxide is used in place of methanol and selected from the list below:

| | |
|---|---|
| a) propylene oxide | h) epifluorohydrin |
| b) epichlorohydrin | i) 7,8-epoxy-2-methyloctadecane |
| c) epibromohydrin | j) epoxy-3 phenoxypropane |
| d) ethylene oxide (under pressure) | k) ethylene glycol diglycidyl ether |
| e) 1,2-epoxybutane | l) polyepoxy resin |
| f) 1,2-epoxydecane | m) mixtures of the above. |
| g) allyl glycidyl ether | |

EXAMPLE 11

Example 2 is modified wherein sufficient methanol is added to the 1A mixture to produce organic silicon-phosphorus chlorides composition with at least two chloride radicals left on each molecule, then the composition is mixed with acetylene in the present of a platinum catalyst to produce an unsaturated organic silicon-phosphorus polymer. The polymer is mixed with a catalytic amount of a free radical initiator, benzoyl peroxide, with it's initiators, thereby producing an organic silicon-phosphorus containing polymer product.

EXAMPLE 12

Example 11 is modified wherein another unsaturated organic compound and a free radical initiator are utilized in place of acetylene and selected from the list below:

| | |
|---|---|
| a) acrylic acid | j) vinyl acetate |
| b) methyl acrylic acid | k) acrolein |
| c) ethyl acrylic acid | l) methyl methacrylate |
| d) acrylonitrile | m) proargyl alcohol |
| e) allyl alcohol | n) linseed oil |
| f) unsaturated polyester resin | o) vinyl pyrrolidone |
| g) isoprene | p) vinyl chloride (pressure) |
| h) chloroprene | q) vinyllidene chloride |
| i) butadiene (pressure) | r) styrene |
| | s) mixtures of the above. |

EXAMPLE 13

Example 2 is modified wherein about equal parts by weight of an epoxy resin and the organic silicon-phosphorus composition of example 2 are mixed and reacted to produce a solid resin.

EXAMPLE 14

About 10 parts by weight of 1B mixture of example 1 and 10 parts by weight of propylene triol are slowly mixed in a cooled container and reacted for about 30 minutes, then 10 parts by weight of propylene oxide are slowly added while agitating thereby producing an organic silicon-phosphorus composition with free hydroxyl groups.

EXAMPLE 15

Example 14 is modified wherein the reactants are mixed in methylene chloride and propylene oxide is replaced with another epoxide selected from the list below;

| | |
|---|---|
| a) ethylene oxide (under pressure) | i) phenyl glycidyl ether |
| b) epichlorohydrin | j) tert. butyl phenyl glycidyl ether |
| c) epoxy-3-phenylpropane | k) cyclohexyl phenyl glycidyl ether |
| d) epibromohydrin | l) polyglycidyl ether of pyrocatechol |
| e) epiflourohydrin | m) polyglycidyl ether of resorcinol |
| f) 1,2-epoxybutane | n) polyglycidyl ether of formaldehyde-phenol |
| g) 1,2-epoxydecane | o) polyglycidyl ether of 1,4-butenediol |
| h) allyl glycidyl ether | p) mixtures of the above. |

EXAMPLE 16

Example 2 is modified wherein mixture 1B is utilized in place of mixture 1A of example 1, and an organic compound selected from the list below is used in place of methanol:

| | |
|---|---|
| a) acetic acid | n) methyl mercapton |
| b) acrylic acid | o) diethylenediamine |
| c) propionic acid | p) urea |
| d) formaldehyde | q) dicyandiamide |
| e) acetoaldehyde | r) melamine |
| f) acetone | s) thiourea |
| g) methanamide | t) carbon disulfide |
| h) propyl amine | u) alginic acid |
| i) phenol | v) aniline |
| j) tolylene diisocyanate | w) tolylene diamine |
| k) dimethyl hydrogen phosphite | x) phthalic acid |
| l) 3-methyl furan | y) furfural |
| m) furfuryl alcohol | z) cellulose | and mixtures of the above.

EXAMPLE 17

Example 2 is modified wherein mixture 1C is used in place of mixture 1A of example 1, and an organic compound selected from the list below is used in place of methanol:

| | |
|---|---|
| a) allyl alcohol | n) benzoic acid |
| b) benzaldehyde | o) aminobenzoic acid |
| c) polyvinyl alcohol | p) sulfamic acid |
| d) acrolein | q) ascorbic acid |
| e) creosote | r) potassium octalate |
| f) castor oil | s) succinic anhydride |
| g) propane diamine | t) fumaric acid |
| h) triethylamine | u) caprolactam |
| i) N-vinyl-2-pyrrolidone | v) diethylene glycol |
| j) tributoxyethyl phosphate | w) lead acetate |
| k) isobutyl vinyl ether | x) ammonium thiocyanate |
| l) methyl magnesium chloride | y) zinc |
| m) dimethyl mercury | z) magnesium | and mixtures of the above.

EXAMPLE 18

About 5 parts by weight of silicon tetrachloride and 5 parts by weight of phosphorus trichloride are mixed in a flask which is in an ice bath, then a mixture of 30 parts by weight of propylene oxide and 30 parts by weight of phthalic anhydride are slowly added and mixed in the flask. Hydrogen chloride evolves from the mixture, then after in about 2–4 hours the mixture is heated to just below the boiling point of the components for 1 to 4 hours thereby producing a flame retardant solid polyester silicon-phosphorus containing product. These products may be used as molding material, coating agents, as flame retardant agents, etc.

EXAMPLE 19

Example 18 is modified wherein the phthalic anhydride is added after the silicon tetrachloride, phosphorus trichloride and propylene oxide are mixed and reacted.

EXAMPLE 20

Example 18 is modified wherein another polycarboxylic acid anhydride and/or acid is utilized in place of phthalic anhydride and selected from the list below:

| | |
|---|---|
| a) phthalic acid | i) glutaric acid |
| b) linoleic acid | j) pimelic acid |
| c) maleic acid | k) oxalic acid |
| d) maleic anhydride | l) isophthalic acid |
| e) fumaric acid | m) terphthalic acid |
| f) succinic acid | n) sebacic acid |
| g) adipic acid | o) ricinoleic acid |
| h) azelaic acid | p) mixtures of the above acids. |

EXAMPLE 21

About 5 parts by weight of silicon tetrachloride and 5 parts by weight of phosphorus trichloride are mixed, then added slowly along with a mixture of 5 parts by weight of glycerol and 30 parts by weight of propylene oxide, to a flask cooled by an ice water bath, while agitating. Hydrogen chloride evolves from the flask. The mixture is allowed to react for 12 to 24 hours, then sodium silicate is added while agitating until the pH is about 7. To this mixture 0.5 parts by weight of dimethylethylamine, 0.2 parts by weight of tin oxalate, 0.5 parts by weight of silicon foam regulator (L6202 by Union Carbide) and 1 part by weight of water are added and mixed, then 45 parts by weight of polymeric MDI (PAPI 27 by DOW) is added and mixed. The mixture expands to produce a flame retardant polyurethane foamed product.

These flame retardant foamed products may be utilized for insulation, sound proofing, construction materials, etc.

EXAMPLE 22

Example 21 is modified wherein another polyisocyanate is used in place of polymeric MDI and selected from the list below:
a) tolylene-2,4-diisocyanate
b) tolylene-2,6-diisocyanate
c) polymethylene polyphenyl polyisocyanate
d) diphenylmethane-4,4-diisocyanate
e) 3-methyldiphenyl-methane-4,4-diisocyanate
f) crude MDI
g) modified polyisocyanate (Mondur PF by Mobay)
h) hexamethylene diisocyanate
i) modified 4,4-diphenylmethane diisocyanate (Mondur CD by Mobay)
J) toluene diisocyanate 80/20 isomer
k) aliphatic diisocyanate (TMI by CYANAMID)
l) ethylene diisocyanate
j) 1,4-tetramethyldissocyanate

EXAMPLE 23

About 5 parts by weight of the silicon tetrachloride, phosphorus trichloride and silicon-phosphorus mixture of example 1A, and 20 parts by weight of caprolactam are slowly added and mixed in a cooled flask. After 6–8 hours the mixture is heated to just below the boiling point of the mixture for 1 to 4 hours thereby producing a solid polyamide silicon-phosphorus containing product.

EXAMPLE 24

Example 23 is modified wherein 10 parts by weight of adipic acid with 10 parts by weight of hexamethylene diamine are utilized in place of caprolactam.

EXAMPLE 25

About 5 parts by weight of Example 1A and 20 parts of propylenediamine are slowly added to a cooled flask while agitating. Hydrogen chloride evolves from the container. The mixture is allowed to react for 6–8 hours, then it is mixed with equal parts by weight of a polyepoxy resin (bisphenol-A-epichlorohydrin) thereby producing a solid flame-retardant epoxy silicon-phosphorus containing product. This product may be used as a flame retardant coating agent, adhesive cavity filler, etc.

EXAMPLE 26

About 20 parts by weight of the phenol silicon-phosphorus compound of example 16i, and 10 parts by weight of aqueous formaldehyde are mixed and heated while agitating at a temperature just below the boiling temperatures of the components for 2–4 hours, thereby producing a solid phenoplast silicon-phosphorus containing product.

EXAMPLE 27

About 20 parts by weight of the urea silicon-phosphorus of example 16p, and 10 parts by weight of aqueous formaldehyde are mixed and heated while agitating at a temperature just below the boiling temperature of the components thereby producing amino-formaldehyde silicon-phosphorus solid product. Other amino silicon-phosphorus compounds selected from examples 16q, 16r, 16s and 16v may be utilized in place of the urea silicon-phosphorus compound to produce amino-formaldehyde silicon-phosphorus solid products.

EXAMPLE 28

Examples 26 and 27 are modified wherein another aldehyde is used in place of formaldehyde and selected from the group listed below:

| | |
|---|---|
| a) acetoaldehyde | e) chloral |
| b) furfural | f) butyraldehyde |
| c) crotonaldehyde | g) acrolein |
| d) paraformaldehyde | h) propionaldehyde | and mixtures of the above.

EXAMPLE 29

Example 3 is modified wherein a compound selected from the list below is reacted with the organic silicon-phosphorus chlorides of example 3, and in the amount of about equal parts by weight thereby producing an organic silicon-phosphorus containing composition:

| | |
|---|---|
| a) propylene glycol | m) allyl alcohol |
| b) acetoaldehyde | n) glycerol |
| c) sodium polysulfide | o) methyl magnesium chloride |
| d) fumaric acid | p) epichlorohydrin |
| e) maleic anhydride | q) propylene oxide |
| f) melamine | r) bis-(n-epoxypropyl)-aniline |
| g) acrylic acid | s) acetylene |
| h) aniline | t) isoprene with a radical initiator |
| i) phenol | u) phosphoric acid |
| j) furfuryl alcohol | v) water |
| k) diethylenetriamine | w) cellulose |
| l) vinyl acetate | x) glycine | and mixtures of the above.

EXAMPLE 30

Example 1A is modified wherein another halide is used in place of chlorine and selected from bromine, fluorine, iodine, hydrogen chloride and hydrogen bromide.

EXAMPLE 31

A mixture of 10 parts by weight of silicon tetrachloride and 20 parts by wight of phosphorus trichloride is slowly added, while agitating, to an excess amount of an organic compound and 30 parts by weight of N,N-dimethylaniline in a cooled flask thereby producing an organic silicon-phosphorus containing composition. The organic compound is selected from the group of compounds consisting of methanol, ethanol, 1-propanol, isopropanol, 1-butanol, furfuryl alcohol, ethylene glycol, propylene glycol, triethylene glycol, tripropylene glycol, glycerol, castor oil, acetic acid, proponic acid, adipic acid, phthalic acid, maleic acid, phthalic anhydride, maleic anhydride, acetic anhydride, acetoamide, proponamide, acetyl chloride, isoprene, ethylene chlorohydrin, phenol, lignin, acetoaldehyde, vinyl ethyl ether, allyl ether, propylene oxide, butylene oxide, furfural, propionaldehyde, acetoaldehyde, acrolein, crotonaldehyde, acetone, methyl ethyl ketone, epichlorohydrin, epibromohydrin, oxalic acid, ethylamine, methylamine, propyl amine, palmitic acid, lanolin, glyceryl tripalmitate, linseed oil, ethyl carbonate, urea, thiourea, melamine, dicyandiamide, guanine, ethylenediamine, propylenediamine, diethylenetriamine, aniline, acetonitrile, acetomide, ethyl cyanide, phenyl isocyanate, ethyl mercaptan, methyl acrylic acid, acrylamide, oleic acid, hydroxyacetic acid, glycolic acid, citric acid, oleic acid, glycine, aminosuccinic acid, cellulose, sucrose, glucose, nitrophenol, tribromophenol, thiophenol, benzenesulfonamide, phenylhydroxyamine, nitrobenzoic acid, benzylamine, nitroaniline, phenylenediamine, cresol, resorcinol, benzylaldehyde, hydroxybenzylaldehyde, acetophenone, benzoic acid, phthalimide, cyclopropane, camphor, oleoresin, furan, tetrahydrofuran, vinylidene cyanide, sodium acrylate, sodium methyl acrylate, methyl vinyl ketone, dimethyl siloxane diols, polyether polyol, polyester polyol, polyamide, unsaturated polyester polyol, unsaturated polyester resin with free acid radicals, sulfosalicylic acid, sodium phenoxide, propylene carbonate, toluene diisocyanate, hexamethylenediamine, sulfonamide, alginic acid, starch, ethyl magnesium chloride, ethylene magnesium chloride, benzyl magnesium bromide, phenyl magnesium chloride and mixtures thereof.

EXAMPLE 32

About equal parts by weight of powdered silicon, powdered phosphorus and a powdered copper catalyst are mixed then heated to just below the boiling point of phosphorus in a closed container, then an excess amount of methyl chloride is passed through the hot powdered mixture thereby producing a mixture of dimethyl dichlorosilane, dimethyl phosphorus chlorides, dimethyl silicon-dimethyl phosphorus chlorides and other organic silicon-phosphorus containing compounds.

EXAMPLE 33

Example 32 is modified wherein the reaction products are slowly added to an excess of methanol in a cooled flask while agitating thereby producing a mixture of organic silicon compounds, organic phosphorus compounds and organic silicon-phosphorus compounds.

EXAMPLE 34

Example 32 is modified wherein the reaction products are hydrolyzed by mixing with a large excess of water thereby producing a mixture of organic silicon compounds, organic phosphorus compounds and organic silicon-phosphorus containing compounds.

EXAMPLE 35

About 10 parts by weight of 1A mixture is mixed with an excess amount of water thereby producing a mixture of silica, polysilicic acid, phosphoric acid and silicon-phosphorus acid.

EXAMPLE 36

Example 35 is modified wherein an aqueous sodium is used in place of water thereby producing sodium silicate, sodium phosphate and sodium silicon-phosphorus compounds.

EXAMPLE 37

About 10 mols of silicon dioxide powder, 10 mols of phosphorus powder and 20 mols of carbon powder are mixed and heated to just below the boiling temperature of phosphorus in a closed container (electric furnace) and the CO is allowed to escape thereby producing a mixture of Si, P and Si—P condensates. An excess of halide selected from the group consisting of chloride, fluoride, bromide and iodide, is passed through the hot mixture thereby producing a mixture of silicon tetrahalide, silicon-phosphorus halide and phosphorus trihalide.

EXAMPLE 38

Example 1A is modified by adding one mol of water for one mol of halide while agitating and utilized in example 2 in place of 1A.

EXAMPLE 39

Example 1B is modified wherein one mol of water for each mol of phosphorus trichloride is added to the mixture while agitating and used in Example 2 in place of 1A.

EXAMPLE 40

Example 1B is modified wherein one mol of phosphorus pentaoxide for 6 mols of phosphorus trihalide is added to the mixture while agitating and used in Example 2.

EXAMPLE 41

Example 37 is modified wherein a metal is used in place of carbon and selected from magnesium and/or zinc.

The following examples, 42–51 utilizes a mixture containing 100 gms of the Si—P halide composition of A–J which is listed below as the silicon-phosphorus halide and 50 gms of N,N-methylaniline. This mixture is gradually added to a cooled flask containing 300 gms of an organic compound or mixtures thereof, listed in the examples below, while agitating, thereby producing an organic silicon-phosphorus containing composition:

A. 10 gms of silicon tetrachloride and 90 gms of phosphorus trichloride;

B. 90 gms of silicon tetrachloride and 10 gms of phosphorus trichloride;

C. 50 gms of silicon tetrachloride and 50 gms of phosphorus trichloride;

D. 50 gms of silicon tetrachloride and 50 gms of phosphorus oxytrichloride;

E. 50 gms of 1A and 50 gms of 1E of example 1;

F. 50 gms of the organic Si—P halide of example 32 and 50 gms of phosphorus oxytrichloride G. 100 gms of the Si—P halide of example 17;

H. 100 gms of the Si—P halide of example 38;

I. 100 gms of the Si—P halide of example 10;

J. 100 gms of the Si—P halide of example 37;

TABLE 1

| | EXAMPLES | | | | |
|---|---|---|---|---|---|
| | 42 | 43 | 44 | 45 | 46 |
| Si—P halide | A | B | C | D | E |
| methanol | 50 gms | | | | |
| ethanol | | | | | 300 gms |
| propylene oxide | 50 gms | 100 gms | 200 gms | 200 gms | |
| glycerol | | | 100 gms | | |
| propylenediamine | 20 gms | | | | |
| ethylene glycol | 80 gms | | | | |
| propylene glycol | | 100 gms | | 100 gms | |
| adipic acid | 100 gms | | | | |
| phthalic anhydride | | 100 gms | | | |

TABLE II

| | EXAMPLES | | | | |
|---|---|---|---|---|---|
| | 47 | 48 | 49 | 50 | 51 |
| Si—P halide | F | G | H | I | J |
| tripropylene glycol | 300 gms | | | | |
| acetic acid | | 100 gms | | | |
| furfural | | 200 gms | | | |
| allyl chloride | | | 150 gms | | |
| epichlorohydrin | | | 150 gms | | |
| acrylonitrile | | | | 200 gms | |
| methy methacrylate | | | | 50 gms | |
| isobutyl vinyl ether | | | | 50 gms | |
| propylene carbonate | | | | | 300 gms |

EXAMPLE 52

100 gms of the silicon-phosphorus chloride A are mixed and reacted with 300 gms of organic phosphorus containing compound thereby producing a solid organic silicon-phosphorus halide. The organic phosphorus containing compound is selected from the group consisting of dimethyl methyl phosphonate, dimethyl hydrogen phosphite, trimethly phosphite, triethyl phosphite, diethyl ethyl phosphonate, triethyl phosphate, triisopropyl phosphite, dibutyl hydrogen phosphite, dibutyl butyl phosphonate, di(2-ethylhexyl) phosphoric acid, melamine hydrogen phosphoric acid, tris(2-chloroethyl) phosphite, phenyl hydrogen phosphate, tris dichloropropyl) phosphate, urea dihydrogen phosphate, ammonium urea hydrogen phosphate, ammonium melamine phosphate, dibutyl pyrophosphoric acid, triphenyl phosphite and mixtures thereof.

These organic silicon-phosphorus compositions may be utilized as flame retardants in plastics, polyurethanes and those soluble in water may be utilized to flame retard wood, cellulose, paper, clothing, to react with organic compounds and many other uses.

EXAMPLE 53

50 gms of silicon-phosphorus halide D and 300 gms of an organic polyether polyol selected from the list below are slowly mixed while agitating, hydrogen chloride evolves from the mixture. The reaction is completed in 1 to 12 hours thereby producing a organic polyether silicon-phosphorus composition. The composition ranges from a clear, thick, liquid polymer to a rubbery solid. The organic polyether polyol are:

a) polypropylene glycol modified with ethylene oxide (Multranol 3900 by Mobay)

b) polypropylene triol, mol. wt. 3000, hydroxyl No. 56 c) propylene oxide/ethylene oxide adduct having a hydroxyl No. 56, mol. wt. 4000 and containing 9% ethylene oxide d) 25% Polybid liquid resin and 75% polyol L56 by ARCO e) polypropylene polyether diol, Hydroxyl No. 112, mol. wt. 1000 f) sucrose/amine polyol, Hydroxyl No. 350 (Poly G 71-357 by OLIN)

g) dibutylene glycol h) triethylene glycol i) polypropylene glycol, mol. wt. 400.

EXAMPLE 54

50 gms of silicon-phosphorus halide C are admixed with 300 gms of polyester resin containing free hydroxyl or carboxylic groups and reacted for 1 to 12 hours at ambient temperature and pressure thereby producing a thick polymer or a rubbery solid. The polyester resin is selected from the list below:

a) unsaturated polyester resin in styrene containing free carboxyl groups (ortho-phthalic resin by KOPPERS), dimethyl ethyl ketone peroxide is added after reaction is completed;

b) diethylene glycol/adipic acid polyester resin with free hydroxyl groups c) glycerol/phthalic anhydride polyester resin with free hydroxyl groups d) flexible unsaturated polyester resin (Polylite Polyester resin 32-367 by REICHHOLD), benzyl peroxide is added after the reaction is completed;

e) phenyl polyester polyol, hydroxyl No. 200 f) aromatic polyester polyol, hydroxyl No. 405

EXAMPLE 55

About 30 parts by weight of silicon-phosphorus halide E are added while agitating to 100 parts by weight of aqueous formaldehyde then 100 parts by weight of amino and/or a phenol compound are added while agitating. The chemical reaction is complete from 5 minutes to 6 hrs thereby producing a solid silicon-phosphorus aminoplast or silicon-phosphorus phenoplast or silicon-phosphorus amino-phenoplast. The amino compound and phenol compound are selected from the following list:

| | |
|---|---|
| a) urea | l) thiourea |
| b) melamine | m) phenol |
| c) dicyandiamide | n) resorcinol |
| d) aniline | o) biuret |
| e) methylurea | p) guanidine |
| f) aminoguanidine | q) cresol |
| g) aminophenol | r) nitrophenol |
| h) bromophenol | s) bisphenol A |
| i) catechol | t) hydroquinone |
| j) 50% phenol & 50% melamine | |
| k) 50% urea & 50% phenol | | and mixtures of the above.

EXAMPLE 56

Example 12 is modified wherein about equal parts by weight of water is added and mixed with the organic compound, then the Si—P halide is added and reacted, then the aqueous formaldehyde is added and reacted.

EXAMPLE 57

An unsaturated organic compound in the amount of 100 gms, 30 gms N,N-dimethylaniline and 50 gms of water are mixed and agitate, and under pressure when a gas is utilized, then 20 gms of the Si—P halide D is slowly added while agitating for 1 to 12 hrs thereby producing an organic silicon-phosphorus containing compound or polymer. The unsaturated organic compound is selected from the group consisting of ethylene, propylene, 1-butene, isobutylene, isoprene, methyl styrene, styrene, acrylonitrile, butadiene, vinyl chloride, vinylidene chloride, vinyl toluene, acrylic acid, methyl acrylic acid, methyl methacrylate, acetylene, vinyl acetate, vinyl toluene, divinyl benzene, rubber latex, isovinyl ether, vinylcyclohexene, isobutyl vinyl ether, isoethyl vinyl ether, cyclooctadiene, N-vinyl-2-pyrrolidone, dicyclopentenyl methacrylate, B-carboxyethyl acrylate and mixtures thereof.

The unsaturated organic compound that can be polymerized by a cationic catalyst or by heat will form an organic silicon-phosphorus polymer. Other catalyst such as free radical catalyst, ionic catalyst and metal catalyst may be added to the water to polymerize the unsaturated compounds that respond to these catalysts thereby producing organic silicon-phosphorus containing polymers.

EXAMPLE 58

About 100 gms of the Si—P halide H and 100 gms of an organometallic compound are mixed and reacted for 1 to 12 hours thereby producing an organic silicon-phosphorus composition. The organometallic compound is selected from the group consisting of sodium acetate, tin octate, dibutyltin oxide, diethyl zinc, ethylmagnesium chloride, tetraethyl lead, methylzinc chloride, butyllithium, diethylmercury, ethyllithium, ethylsodium, butyleneborane, isobutylaluminum, ethylaluminum, calcium carbide, sodium cyanide, potassium cyanide, calcium cyanide and mixtures thereof.

I claim:

1. An organic silicon-phosphorus containing resinous composition prepared by the process steps of:
   A. mixing and heating the following compounds:
      a) silicon compound
      b) phosphorus compound; then
   B. admixing and reacting with:
      a) halide;
         thereby producing a mixture of silicon-phosphorus halides, silicon halides and phosphorus halides; then
   C. admixing and reacting with the following components:
      a) organic compound that will react with a silicon halides, silicon-phosphorus halides and/or phosphorus halides in an amount to where there are halides and/or organic radicals with active hydrogens and/or metal radicals remaining thereby producing an organic silicon-phosphorus containing compound; then
   D. admixing and reacting with the following components:
      a) saturated or unsaturated organic compound and/or organo-metallic compound that will react with an organic silicon-phosphorus containing compound by the process of condensation or addition to form a resinous composition;
      b) basic salt forming compound; 0 to 300 parts by weight; then with
      c) water; 0 to 400 parts by weight;
   E. polymerize by means that will complete the condensation and/or addition process thereby producing an organic silicon-phosphorus containing resinous composition.

2. An organic silicon-phosphorus containing composition of claim 1 wherein the organic compound is selected from the list consisting of substituted or unsaturated or saturated alcohols, polyalcohols, epoxides, epihalohydrins, polyepoxides, organic acids and anhydrides, polycarboxylic acids and anhydrides, isocyanates, polyisocyanates, thioalcohols, phenols, phenoplasts, thiophenols, aldehydes, halogenated alcohols and polyalcohols, halogenated organic acids and polycarboxyl acids, sulphonic acid chlorides, organic esters, ethers, polyethers, polyesters, thioethers, ketones, nitrides, sulphonic acids, amines, polyamines, alkenes, alkynes, arylalkenes, organic polyenes, aminophenols, organic phosphates, organic phosphites, organic phosphonates, organic phosphines, carbohydrates, lignin, cellulose, terpenes, oils, fats, amides, polyamides, aminoalcohols, amino compounds, aminoplasts, imides, polyimides, Grignard reagents, organo-metallic compounds, alkyl carbonates and mixtures thereof.

3. The organic silicon-phosphorus containing resinous composition of claim 1, wherein the polymerization means is selected from the group consisting of heat, catalyst, ultra violet light, free radicals initiators, redox system, air, water and mixtures thereof.

4. An organic silicon-phosphorus containing resinous composition of claim 1 wherein the halide is selected from group the consisting of chloride, bromide, fluoride, iodide, hydrogen chloride, hydrogen bromide, hydrogen fluoride and mixtures thereof; in the amount of 4 mols of halide or more for each mol of silicon and 3 to 5 mols of halide for each mol of phosphorus.

5. An organic silicon-phosphorus containing resinous composition prepared by the following steps:
   A. mixing the following components:
      a) silicon tetrahalide, 10 to 100 parts by weight;
      b) phosphorus trihalide, 10 to 100 parts by weight;
   B. admixing and reacting the following components:
      a) organic compound that will react with a silicon halides, silicon-phosphorus halides and/or phosphorus halides; in an amount to wherein there are halide atoms and/or organic radical with active hydrogens left on the organic silicon-phosphorus containing compound; then
   C. admixing and reacting the following components:
      a) saturated or unsaturated organic compound that will react with the organic silicon-phosphorus containing compound to produce a resinous composition; then
   D. polymerize by means that will complete the polymerization.

6. An organic silicon-phosphorus containing resinous composition of claim 1 wherein the organic compound contain one or more of the following radicals:

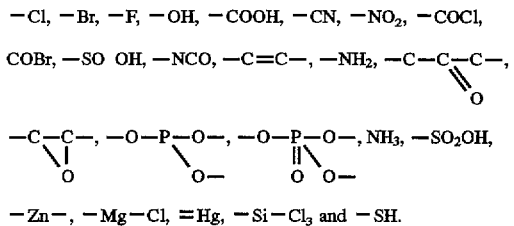

7. An organic silicon-phosphorus containing resinous composition of claim 1 wherein the basic salt forming compound is selected from the group consisting of compounds containing alkali metals, alkaline earth metals, metals, ammonia radicals, amines, polyamines, amino compounds, aminoplasts and mixtures thereof.

8. An organic silicon-phosphorus containing resinous composition of claim 1 which contains halide atoms; an amount of the organic compound is utilized wherein there are halide atoms left on the organic silicon-phosphorus composition.

9. An organic silicon phosphorus containing resinous composition of claim 8 wherein an organic compound of claim 1 which contains more than one active hydrogen is reacted with the organic silicon-phosphorus halide composition of claim 8 in an amount to react with all of the halide atoms.

10. An organic silicon-phosphorus containing resinous composition of claim 1 wherein the basic salt forming compound is added with the organic compound of claim 1.

11. The organic silicon-phosphorus containing resinous composition of claim 1 wherein water is added with the organic compound of claim 1.

12. The silicon-phosphorus halide of claim 1 with the general formula of:

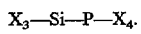
$X_3$—Si—P—$X_4$.

13. The organic silicon-phosphorus composition of claim 1 with the general formula of:

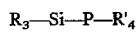
$R_3$—Si—P—$R'_4$ wherein R and R' are organic radicals selected from the reaction product of the organic compounds of claim 1.

14. The organic silicon-phosphorus containing resinous composition of claim 5 wherein the organic compounds of claim 5 is reacted with all of the halide atoms.

15. The organic silicon-phosphorus containing resinous composition of claim 5 wherein additional different organic compounds containing two or more active hydrogens of claim 5 is reacted with the organic silicon-phosphorus containing compound containing halide.

16. An organic silicon-phosphorus containing resinous composition prepared by the following steps:
   A. mixing the following components:
      a) silicon tetrahalide
      b) phosphorus oxytrihalide
   B. admixing and reacting the following components:
      a) organic compounds that will react with silicon tetrahalide, silicon-phosphorus halide and/or phosphorus oxytrihalide in an amount to where there are halide atoms left on the organic silicon-phosphorus containing compound; then
   C. admixing and reacting the following components:
      a) saturated or unsaturated organic compound that will react with and polymerize by a process of condensation or addition; then
   D. polymerize by means that will complete the polymerization to produce a resinous composition.

17. An organic silicon-phosphorus containing resinous composition of claim 16 which contains halogen atoms.

18. An organic silicon-phosphorus containing resinous composition of claim 17 wherein the organic silicon-phosphorus containing compound contains halogen atoms is reacted with organic compounds selected from the group consisting of polyhydroxy compounds, polyepoxies, polycarboxylic acids, polycarboxylic anhydrides, polyamines, aldehydes with phenols, aldehydes with amino compounds, polyisocyanates, furfuryl alcohol, furfural and mixtures thereof.

19. An organic silicon-phosphorus containing resinous composition of claim 5 wherein the organic compound is an organometallic compound selected from the group consisting of alkyl alkali metals, dialkylzinc, dialkylmercury, alkylene borone, alkylaluminium, calcium carbide, alkali metal cyanide, alkaline earth metal cyanide, alkali metal salts of carboxylic acids, alkali metal salts of polycarboxylic acids, alkyloxyalkali metals, tin salts of carboxylic acids, zinc salts of carboxylic acids and mixtures thereof.

20. A process for the production of organic-silicon containing resinous composition prepared by the process steps of:
   A. mixing and heating the following compounds;
      a) silicon compound; 10 to 100 parts by weight
      b) phosphorus compound; 10 to 100 parts by weight then
   B. admixing and reacting with:
      a) halide; in an amount of 4 or mols of halide to 1 mol of silicon, 3 to 5 mols of halide to 1 mol of phosphorus; then
   C. admixing and reacting with:
      a) saturated and/or unsaturated organic compound and/or an organo-metallic compound that will react with a silicon halides, silicon-phosphorus halides and/or phosphorus halides in an amount to where them are halide atoms and/or radicals with active hydrogens left on the organic silicon-phosphorus containing compound; then
   D. admixing and reacting with:
      a) saturated and/or unsaturated organic compound and/or an organo-metallic compound that will react with organic silicon-phosphorus containing compounds to produce a resinous composition;
      b) basic salt forming compound; 0 to 300 parts by weight; then
      c) water; 0 to 400 parts by weight; then
   E. Polymerizing by means that will complete the condensation and/or addition to produce an organic silicon-phosphorus containing resinous composition.

21. The organic silicon-phosphorus containing resinous composition of claim 1 with the general formula of:

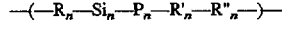
—(—$R_n$—$Si_n$—$P_n$—$R'_n$—$R''_n$—)— wherein n is a number 1–4, R, R' and R" are organic radicals with 1–20 carbon atoms.

* * * * *